US00PP18708P2

(12) United States Plant Patent
Bradford

(10) Patent No.: US PP18,708 P2
(45) Date of Patent: Apr. 1, 2008

(54) NECTARINE TREE NAMED 'JUNE BRIGHT'

(50) Latin Name: *Prunus persica*
Varietal Denomination: June Bright

(76) Inventor: Lowell Glen Bradford, 10237 E. Mariposa Way, LeGrand, CA (US) 95333

( * ) Notice: Subject to any disclaimer, the term of this patent is extended or adjusted under 35 U.S.C. 154(b) by 0 days.

(21) Appl. No.: 11/637,887

(22) Filed: Dec. 13, 2006

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP7,066 P 12/1989 Bradford
PP7,421 P 1/1991 Bradford
PP9,495 P 4/1996 Bradford

*Primary Examiner*—Kent Bell

(57) ABSTRACT

The present invention relates to a nectarine tree, *Prunus persica,* and more particularly to a new and distinct variety broadly characterized by a medium size, vigorous, hardy, self-fertile, productive and regular bearing tree. The fruit matures under the ecological conditions described in mid June, with first picking on Jun. 14, 2006. The fruit is uniformly large in size, mildly acidic and sweet in flavor, globose in shape, clingstone in type, very firm in texture, yellow in flesh color, and full dark red in skin color.

1 Drawing Sheet

Botanical classification: *Prunus persica.*
Variety denomination: 'JUNE BRIGHT'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'JUNE BRIGHT'. The present variety was hybridized by me in 1996, grown as a seedling on its own root in my greenhouse, and transplanted to a cultivated area of my experimental orchard near Le Grand, Calif., in Merced County (San Joaquin Valley).

The variety was developed as a first generation cross using 'Diamond Princess' (U.S. Plant Pat. No. 7,066) peach as the selected seed parent and 'Rose Diamond' (U.S. Plant Pat. No. 7,421) nectarine as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed parent, 'Diamond Princess' peach, by producing fruit that is nearly globose in shape, yellow in flesh color, and full red in skin color, but is quite distinguished therefrom by producing fruit that is nectarine instead of peach, that is clingstone instead of freestone, and that matures about four weeks earlier.

The present variety is similar to its selected pollen parent, 'Rose Diamond' nectarine, by producing nectarines that are nearly globose in shape, firm in texture, and yellow in flesh color, but is distinguished therefrom by producing fruit that is larger in size, darker red in skin color, and that mature about three weeks later.

The present variety is most similar to 'Diamond Bright' (U.S. Plant Pat. No. 9,495) nectarine, by producing nectarines that mature in early to mid June, that are nearly globose in shape, very firm in texture, yellow in flesh color, and full red in skin color, but is distinguished therefrom by producing fruit that is larger in size and firmer in texture.

SUMMARY OF VARIETY

In summary, the present variety is characterized by a medium size, vigorous, hardy, self-fertile, productive and regular bearing tree. The fruit matures under the ecological conditions described in mid June, with first picking on Jun. 14, 2006. The fruit is uniformly large in size, mildly acidic and sweet in flavor, globose in shape, clingstone in type, very firm in texture, yellow in flesh color, and fully dark red in skin color.

DRAWING

The accompanying photograph consists of four whole fruits positioned to display the characteristics of the skin color and form, one fruit divided transversely to the suture plane to reveal the flesh and stone, two insets to reveal buds and blossoms in various stages, various leaves, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 18, 2006, on the original tree during its tenth growing season. All major color code designations are by reference to the Inter-Society Color Council, National Bureau of Standards. Common color names are also used occasionally.

Tree

Size: Medium, reaching and maintaining a height of 10' [3.05 m.] and a spread of 10' [3.05 m.] after ten growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer, with no alternate bearing yet observed.

Approximate chilling requirement: 700 hours.

Trunk:

*Size.*—Medium, reaching a maximum diameter of 4¾" [121 mm.] after the tenth growing season.

*Texture.*—Shaggy.

*Bark color.*—A Moderate olive brown [95. m.OlBr] and Deep brown [56. deep Br] variegation.

*Lenticels.*—Approximate Number Per Square Inch: 8. Color: Deep orange yellow [69. deep OY]. Typical Size: 3/16" [4.8 mm.] to 7/16" [11.1 mm.]. Shape: Eye-shaped to elongated.

Branches:

*Size.*—Diameter of limb is 2⅞" [73 mm.] measured 12" above the crotch, 1¾" [44 mm.] measured 12" above the first fork.

*Texture.*—Smooth on first and second year wood, increasing roughness with age.

*Color.*—1st Year Wood Topside: Grayish red [19. gy./R]. 1st Year Wood Underside: Brilliant yellow green [116. brill.YG]. Older Wood: Deep yellowish brown [75. deep yBr].

*Lenticels.*—Number Per Square Inch: More than 30 on second year wood. Color: Moderate orange yellow [71. m.OY]. Typical size: 1/32" [0.8 mm.] to 3/32" [2.4 mm.] on second year wood. Shape: Elongated.

Leaves:

*Size.*—Medium. Average Length: 5¾" [146 mm.]. Average Width: 1¾" [44 mm.].

*Arrangement.*—Alternate.

*Thickness.*—Medium.

*Form.*—Elliptical.

*Apex.*—Acuminate.

*Base.*—Acute with an average angle of 75 to 85 degrees.

*Surface.*—Smooth.

*Color.*—Dorsal Surface: Dark yellowish green [137. d.yG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ⅜" [9.5 mm.]. Average Thickness: 1/16" [1.6 mm.]. Color: Strong yellow green [117. s.YG].

*Stipules.*—Number: 2 to 6 per growing tip. Average Length: 5/16" [7.9 mm.]. Color: Very yellow green [115. v.YG] becoming Moderate reddish brown [43. m.rBr] with maturity.

*Glands.*—Number: Mostly 2 to 4. Position: Alternately positioned on the petiole and the base of blade. Size: Medium. Form: Reniform. Color: Strong yellow green [117. s.YG] turning Moderate reddish brown [43. m.rBr] with age.

*Leaf buds.*—Pointed, medium in size.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Light purplish pink [249. lpPk].

Flowers: Perfect, complete, perigynous, usually a single pistil, typically thirty or more stamens, five sepal and petal locations alternately positioned.

*Type.*—Showy, large.

*Average flower diameter.*—1 13/16" [46.0 mm.].

*Number of petals.*—Usually five, but 50% contain extra petal fragments with 25% being full double blossoms.

*Petal shape.*—Circular to oval.

*Petal margin.*—Somewhat wavy.

*Average petal diameter.*—11/16" [17.5 mm.].

*Average petal length.*—¾" [19.1 mm.].

*Petal apex.*—Rounded.

*Petal base.*—Rounded to somewhat truncate.

*Petal color.*—Pale pink [7. p.Pk] toward the apex, Light pink [4. l.Pk] toward the base.

*Anther color.*—Moderate reddish orange [37. m.rO] over a Light yellow [86. l.Y] center at bloom onset.

*Stigma color.*—Light greenish yellow [101. l.gY].

*Sepal color.*—Dark purplish red [259. d.pR].

*Sepal length.*—¼" [6 mm.].

*Sepal width.*—3/16" [5 mm.].

*Average pistil length.*—11/16" [17.5 mm.].

*Average stamen length.*—9/16" [14.3 mm.].

*Fragrance.*—Moderate.

*Blooming period.*—Medium, two days after 'Spring Bright' (U.S. Plant Pat. No. 7,507) nectarine.

*Onset of bloom.*—One percent on Feb. 27, 2006.

*Date of full bloom.*—Mar. 9, 2006.

*Duration of bloom.*—One to two weeks, dependent on ambient temperature.

*Number per cluster.*—1 to 3 with single flowers most common.

FRUIT

Maturity when described: Firm ripe, Jun. 18, 2006.

Date of first picking: Jun. 14, 2006.

Date of last picking: Jun. 23, 2006.

Size: Uniform, large.

*Average diameter axially.*—2 13/16" [71.4 mm.].

*Average diameter across cheek plane.*—2⅞" [73.0 mm.].

*Average diameter across future plane.*—2⅞" [73.0 mm.].
*Typical weight.*—7.0 ounces [198 grams].
Form: Globose, slightly asymmetrical.
*Longitudinal section form.*—Oval.
*Transverse section through diameter.*—Round.
Suture: A sharp groove near the base, shallow along the sides, sharp near the apex, and terminating into a slight depression just past the pistil point.
Ventral surface: Rounded, mostly lipped throughout.
Lips: Somewhat unequal.
Cavity: Flaring, elongated in the suture plane, suture showing on one side, light yellow [86. l.Y] stem markings typical.
*Depth.*—⅜" [9.5 mm.].
*Breadth.*—1¼" [31.8 mm.].
Base: Truncate, but cordate if viewed parallel to the suture.
Apex: Rounded to slightly cordate.
Pistil point: Both apical and oblique, short.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Astringent.
*Tendency to crack.*—Slight in wet season.
*Color.*—Very deep red [14. v.deep R] over a Moderate red [15. m.R] background with moderate Light yellow [86. l.Y] freckling toward the apex.
Flesh:
*Color.*—Brilliant Yellow [83. brill.Y] with the slightest bit of Strong red [12. s.R] flecking next to the skin.
*Surface of pit cavity.*—Light yellow [86 l.Y] fibers broken when twisted from the stone.
*Amygdalin.*—Abundant to moderate.
*Juice.*—Moderate, rich.
*Texture.*—Firm, crisp, melting.
*Fibers.*—Abundant, fine.
*Ripens.*—Earlier at the apex.
*Flavor.*—Acidic and sweet, typically 13 brix.
*Aroma.*—Moderate.
*Eating quality.*—Good.

STONE

Type: Clingstone.
Form: Oval.
Hilum: Narrow, oblong.
Base: Straight, rounded.
Apex: Acuminate, with an average tip angle of 70 degrees and a tip of length ⅛" [3.2 mm.].
Sides: Slightly unequal.
Surface: Regularly furrowed horizontally near the apex and along the ventral edge, pitted toward the base.
Ridges: Rounded.
External color: Dark orange yellow [72. d.OY].
Pit wall color when cracked: Light orange yellow [70. l.OY].
Cavity surface color: Light yellowish brown [76. l.yBr].
Average pit wall thickness: ¼" [6.4 mm.].
Average width: ¼" [31.8 mm.].
Average length: 1⅝" [41.3 mm.].
Average breadth: ¾" [19.1 mm.].
Tendency to split: Slight.
Kernel:
*Form.*—Oval.
*Skin color.*—Brilliant yellow [83. brill.Y] when first removed.
*Pellicle color.*—Grayish yellow [90. gy.Y].
*Vein color.*—Grayish yellow [90. gy.Y].
*Taste.*—Sweet.
*Viable.*—Yes.
*Average width.*—9/16" [14.3 mm.].
*Average length.*—¾" [19.1 mm.].
*Amygdalin.*—Scant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Diamond Bright' (U.S. Plant Pat. No. 9,495) nectarine by producing nectarines that mature in early to mid June, that are nearly globose in shape, very firm in texture, yellow in flesh color, and full red in skin color, but is distinguished therefrom by producing fruit that is larger in size and firmer in texture.

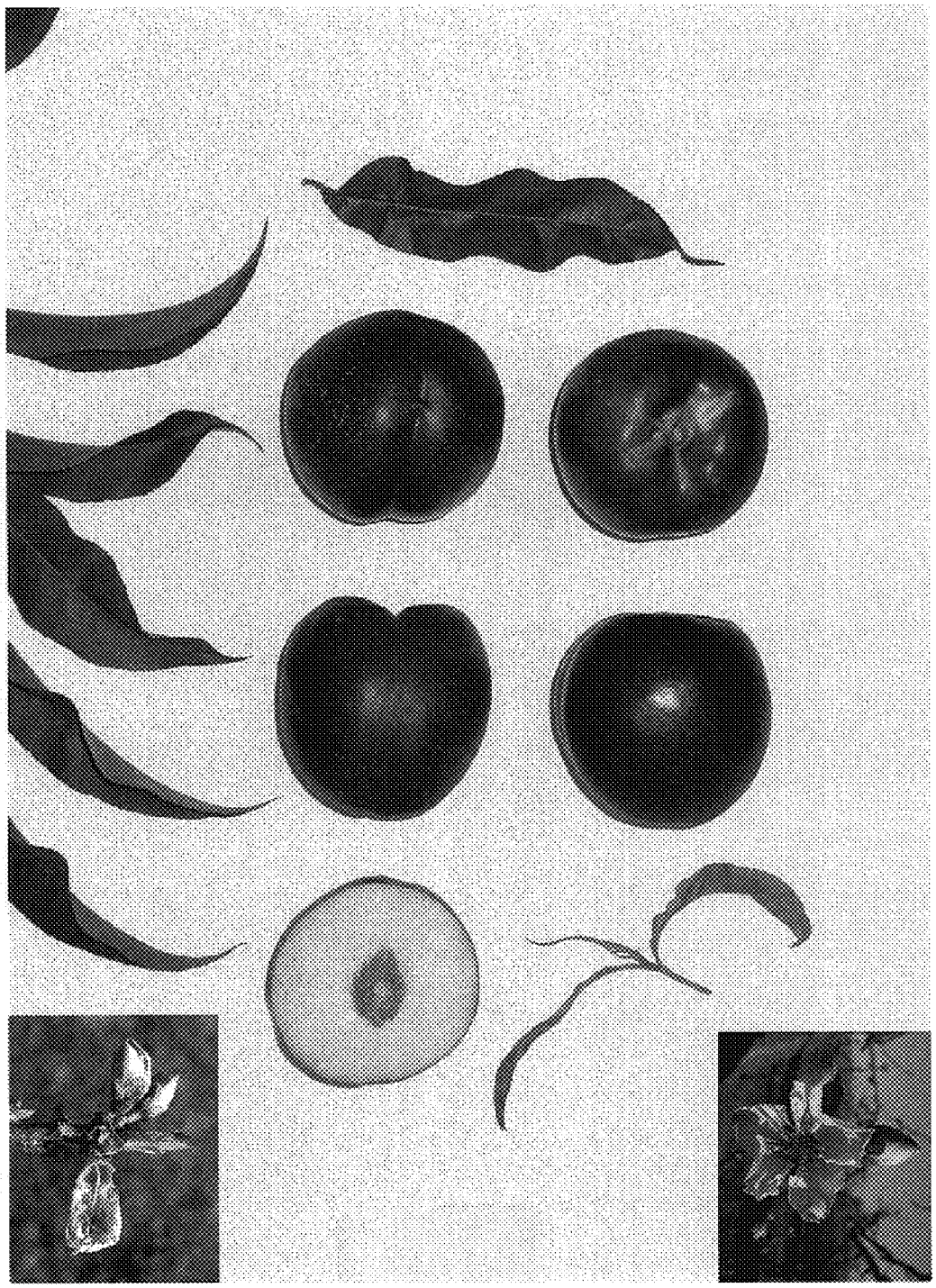

* * * * *